United States Patent
O'Brien et al.

[11] 4,003,244
[45] Jan. 18, 1977

[54] ULTRASONIC PULSE-ECHO THICKNESS MEASURING APPARATUS

[75] Inventors: Patrick M. O'Brien, Stratford; Richard J. Pittaro, Stamford; Philip A. Walker, Trumbull, all of Conn.

[73] Assignee: Krautkramer-Branson, Incorporated, Stratford, Conn.

[22] Filed: Sept. 30, 1975

[21] Appl. No.: 618,073

[52] U.S. Cl. .................................. 73/67.8 R
[51] Int. Cl.² ..................................... G01N 29/00
[58] Field of Search ............... 73/67.8 R, 67.9, 67.7, 73/67.5 R; 340/1 R, 5 R, 5 C; 324/83 R, 83 FE

[56] References Cited
UNITED STATES PATENTS

| | | | |
|---|---|---|---|
| 2,418,538 | 4/1947 | Yetter | 73/67.7 |
| 3,048,031 | 8/1962 | Beaujard et al. | 73/67.9 |
| 3,576,126 | 4/1971 | Weighart | 73/67.7 |
| 3,690,153 | 9/1972 | Matay | 73/67.8 R |
| 3,774,717 | 11/1973 | Chodorow | 73/67.7 |

*Primary Examiner*—Donald O. Woodiel
*Assistant Examiner*—Stephen A. Kreitman
*Attorney, Agent, or Firm*—Ervin B. Steinberg; Philip J. Feig

[57] ABSTRACT

An electrical circuit incorporated in a receiver circuit of an ultrasonic pulse-echo thickness and/or velocity measuring apparatus causes the entrant surface and rear wall responsive video signals to be of equal magnitude and in phase with each other. The provision of echo responsive video signals having equal amplitude and phase results in a measuring apparatus exhibiting improved accuracy while requiring fewer and less expensive circuit components.

6 Claims, 4 Drawing Figures

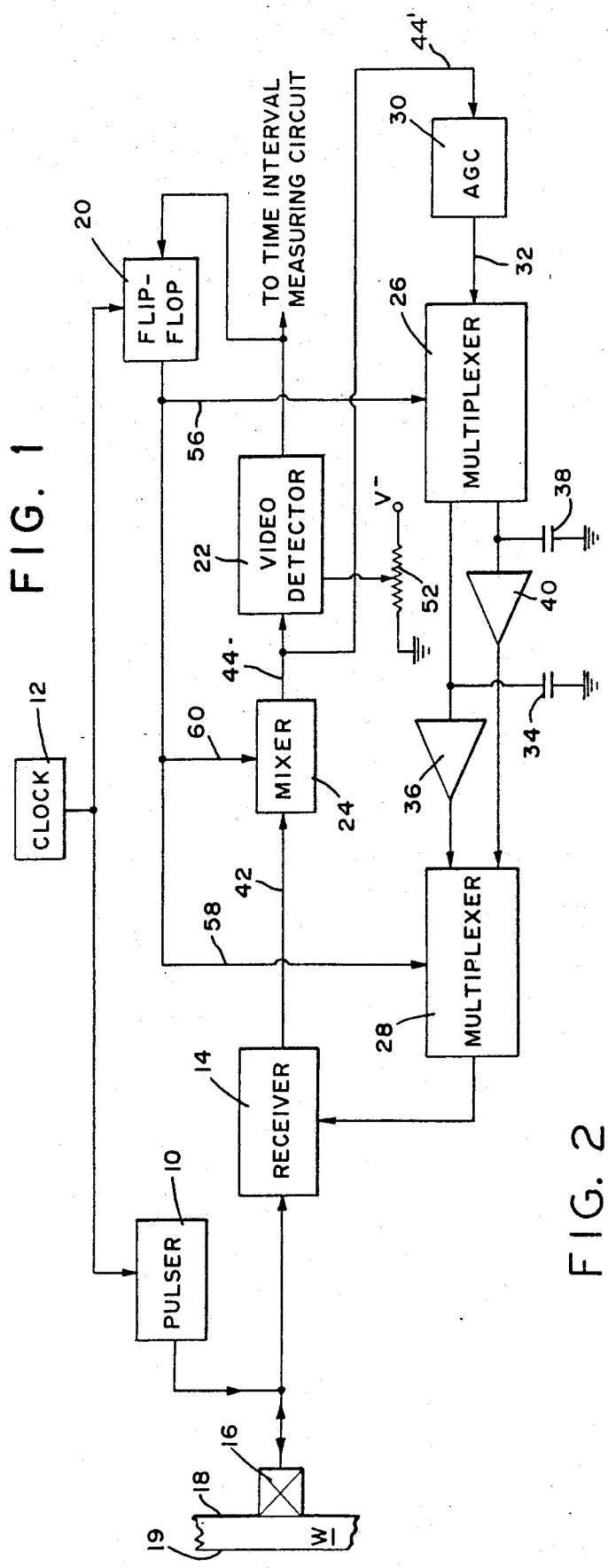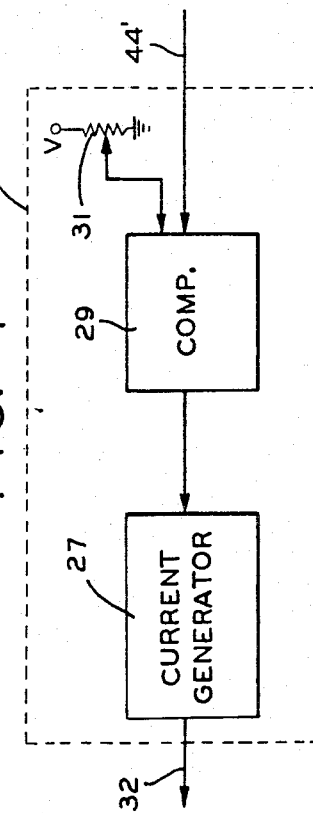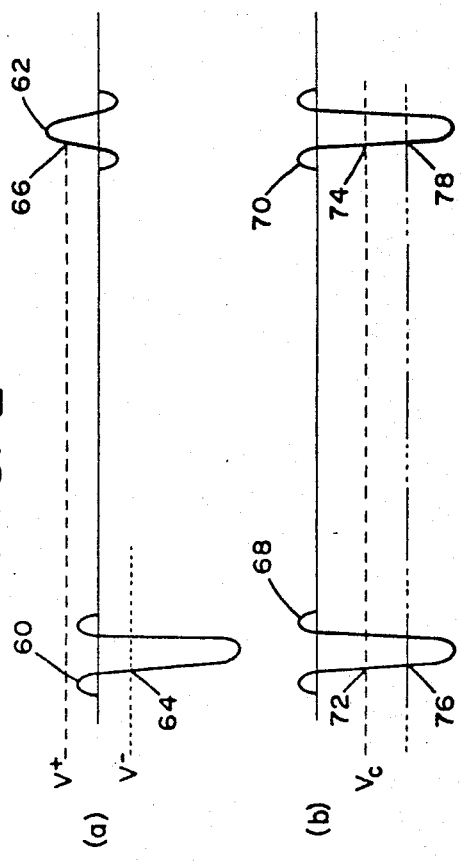

ULTRASONIC PULSE-ECHO THICKNESS MEASURING APPARATUS

BRIEF SUMMARY OF THE INVENTION

The present invention concerns an electrical circuit for an ultrasonic thickness and/or velocity measuring apparatus. Specifically, the disclosed electrical circuit when incorporated in a receiver circuit of an ultrasonic thickness measuring apparatus causes the entrant surface responsive echo signal and the rear wall responsive echo signal to be of equal magnitude and in phase with each other.

In pulse-echo ultrasonic thickness measuring apparatus a piezoelectric transducer probe, acoustically coupled to a workpiece by water, oil or other suitable couplant, is periodically energized for transmitting ultrasonic energy search signals into the workpiece. A portion of the transmitted ultrasonic energy upon intercepting an acoustic discontinuity, such as the entrant surface or rear wall of the workpiece, is reflected back towards the transducer probe. A measurement of the time interval between the receipt of an entrant surface responsive echo signal and a rear wall responsive echo signal yields a value commensurate with the thickness and acoustic velocity of the workpiece. The relationship between the time interval measurement and the workpiece characteristic is that the thickness of a workpiece equals the product of the velocity of ultrasonic energy traveling through the workpiece times one-half the measured time interval.

In employing pulse-echo ultrasonic techniques to determine the thickness of a workpiece two problems arise. The first problem concerns the ultrasonic signal attenuation due to the length of the path through which the signal must travel, i.e., the thickness of the workpiece. The other problem concerns the phase difference between the echo signals responsive to the ultrasonic energy reflected at the entrant surface and the ultrasonic energy reflected at the rear wall of the workpiece. The signal attenuation is caused largely by the grain structure and porosity of the workpiece. In prior apparatus a gain control circuit is combined with the receiver circuit to increase the gain (amplification) of the receiver circuit commensurate with the thickness of the workpiece. The use of gain control circuits has met with general success in overcoming the attenuation problem, but the problem of the time interval measurement error resulting from a phase difference between the two mentioned signals has not been satisfactorily solved.

When an ultrasonic energy signal intercepts an acoustic discontinuity disposed normal to the signal path and characterized by a higher acoustic impedance than that of the preceding path, a portion of the ultrasonic energy is reflected back towards the transmit receive transducer probe. The reflected signal, in such instance, is phase inverted with respect to the transmitted signal. When an ultrasonic energy signal intercepts an acoustic discontinuity of lower acoustic impedance no phase shift occurs. Hence, a signal refelected from the entrant surface and a signal reflected from the rear wall of a workpiece will exhibit a phase difference relative to each other of 180°. For a detailed description of phase inversion see, for instance, chapter two of the book "Ultrasonics" by D. Ensminger, Marcel Dekker, Inc., New York, 1973. In prior apparatus, two complementary circuits, a negative signal detection circuit and a positive signal detection circuit have been required to process the phase difference between the signal reflected from the entrant surface and rear wall of a workpiece. A first negative signal detection circuit is used to provide an output pulse when the negative going signal is more negative than a first determined negative threshold value and a complementary positive signal detection circuit is used to provide an output pulse when the positive going signal exceeds a second predetermined positive threshold value. The time interval between the two output pulses from the detection circuits is measured by means well known in the art and processed for displaying a value commensurate with the workpiece thickness.

Since prior circuits process both a positive going and a negative going echo responsive video signal, two gain control circuits are required. One gain control circuit being associated with each polarity signal. The disclosed invention obviates the requirement of two detection circuits and two gain control circuits by automatically shifting the phase of one of the echo responsive signals by 180 degrees resulting in both echo responsive signals being of the same polarity.

A single electrical circuit is used for detecting the receipt of both the positive and negative going echo responsive signals. A video detector circuit provides a signal indicating that a first echo responsive video signal having an amplitude greater than a predetermined threshold value has been received. The signal triggers switching means to cause the receiver means to shift the phase of a subsequently received video signal by 180°. The subsequently received video signal is then in phase with the first video signal and the video detector circuit detects the receipt of the subsequently received video signal when the amplitude exceeds the same predetermined threshold value. Moreover, the electrical circuit includes automatic gain control means for causing the amplitude of successive signals to be of the same predetermined amplitude. In this manner, the linearity of each signal is the same so that the time interval measured between the successive signals reaching a predetermined threshold value is fixed even when the absolute value of the predetermined threshold level varies.

A principal object of the present invention is, therefore, the provision of an electrical circuit for a pulse-echo ultrasonic thickness measuring apparatus providing improved accuracy.

Another principal object of the present invention is the provision of an electrical circuit for a pulse-echo ultrasonic thickness measuring apparatus requiring fewer circuit components.

A further object of the present invention is the provision of an electrical circuit for a pulse-echo ultrasonic thickness measuring apparatus which provides a 180° phase shift of a selected acoustic discontinuity responsive video signal.

A still further object of the present invention is the provision of an electrical circuit for a pulse-echo ultrasonic thickness measuring apparatus which provides automatic gain control and 180° phase shift of acoustic discontinuity responsive video signals.

Further and still other objects of the present invention will become apparent when the specification is read in conjunction with the accompanying drawings.

BRIEF DESCRIPTION OF THE DRAWINGS

FIG. 1 is a schematic electrical circuit block diagram of a preferred embodiment of the invention;

FIG. 2 is a graphical representation of signal waveforms within the circuit per FIG. 1;

FIG. 4 is a schematic electrical circuit block diagram of a portion of the circuit per FIGS. 1 and 3.

DETAILED DESCRIPTION OF THE INVENTION

Figure 3:
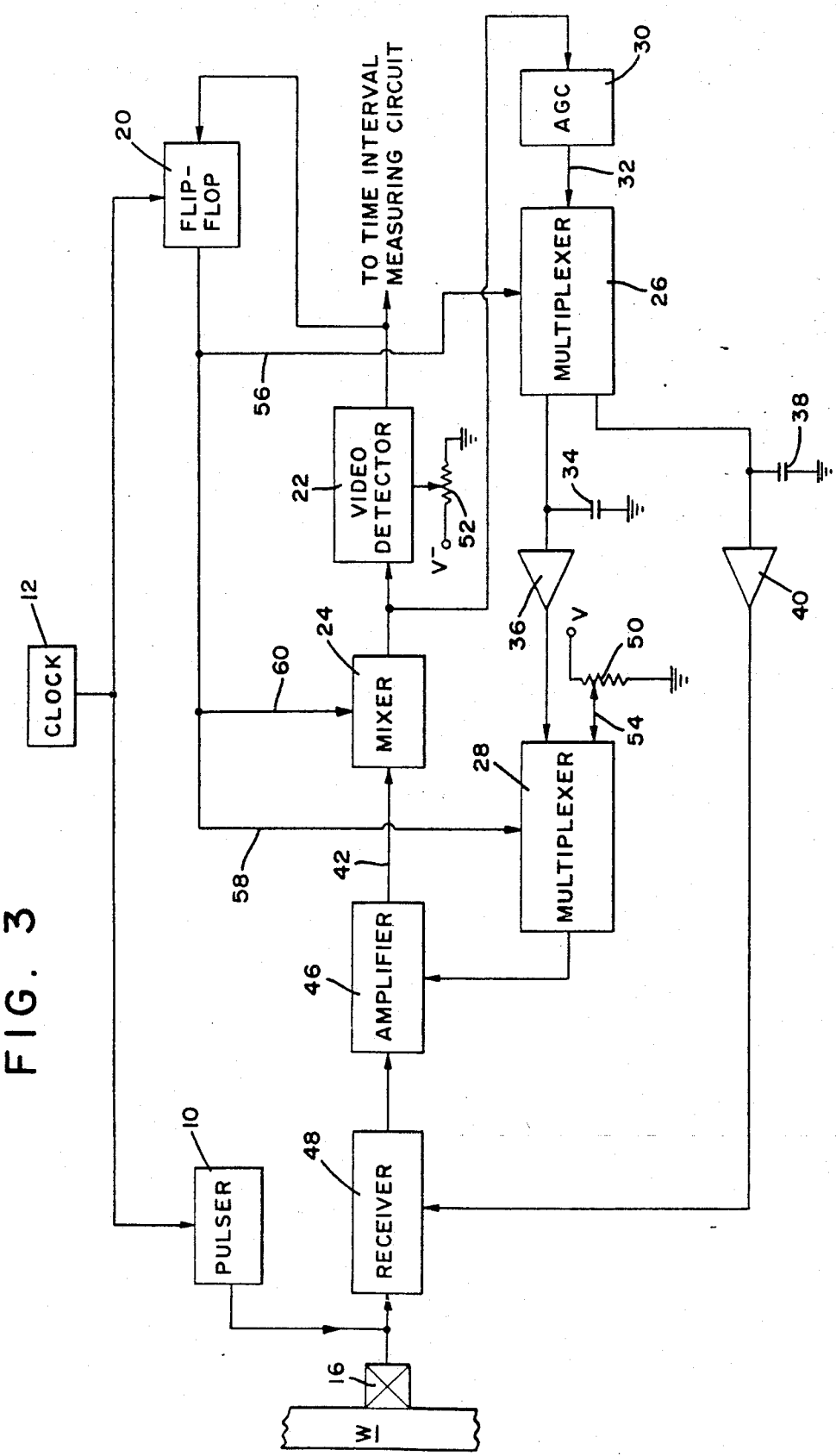
FIG. 3 is a schematic electrical circuit block diagram of an alternative embodiment of the invention.

Referring now the figures and FIG. 1 in particular, there is shown an electrical circuit which shifts the phase of selected echo responsive video signals by 180° and causes successive echo responsive video signals to be of a constant amplitude. Pulser circuit 10, responsive to the receipt of timing pulses from clock 12, cyclically provides output signals to a transmit-receive piezoelectric transducer probe 16. Responsive to the receipt of an output signal from pulser circuit 10, the transducer probe 16, acoustically coupled to a workpiece W via water, oil or other suitable couplant, transmits an ultrasonic energy search signal into the workpiece W.

A first portion of the ultrasonic energy search signal, upon intercepting an acoustic discontinuity, such as the workpiece entrant surface 18, is reflected back through the couplant to the probe 16. The phase of the reflected signal is shifted by 180° from the phase of the transmitted signal. A second portion of the transmitted search signal upon intercepting a second acoustic discontinuity, such as the rear wall 19 of workpiece W, is partially reflected back through the workpiece W and couplant to the probe 16. The phase of the rear wall responsive echo signal is substantially the same as the phase of the transmitted signal.

In FIG. 2, trace a is a graphical representation of the echo signals received by the transducer probe 16. Waveform 60 is the phase inverted entrant surface responsive echo signal and waveform 62 is the rear wall responsive echo signal. Waveform 62 is 180 degrees out of phase with respect to the waveform 60 and of a smaller amplitude due to the attenuation of the ultrasonic signal traveling twice the distance through the workpiece W.

In prior pulse-echo ultrasonic thickness measuring apparatus it has been common practice to use two video detector circuits having a threshold level at V⁻ and V⁺ respectively for measuring the time interval between the points 64 and 66 of the echo responsive signals. The first video detector provided a first electrical pulse when the signal represented by waveform 60 becomes equal to or more negative than the threshold level V⁻ at point 64, and a second video detector provided a second electrical pulse when the signal represented by waveform 62 assumed a value equal to or more positive than the threshold level V⁺ at point 66. The time interval between the first and second pulses is measured by known means for providing a value commensurate with the workpiece thickness.

In the present embodiment, as shown in FIG. 1, only one video detector circuit 22 is required for obtaining signals commensurate with the time required for the ultrasonic energy search pulse to travel through the workpiece. The clock 12, in addition to providing timing signals to pulser circuit 10, also provides a reset signal to flip-flop circuit 20 for causing the flip-flop circuit to be in its initial condition. The flip-flop circuit 20, when triggered by a signal from the video detector circuit 22 changes from its initial condition, and provides a signal causing the mixer circuit 24 to shift the phase of subsequently received video signals by 180 degrees and causing multiplexers 26 and 28 to change conditions as will be explained below. Moreover, an automatic gain control circuit 30 (AGC) is provided for automatically adjusting the gain (amplification) of the receiver circuit 14 so that the amplitude of each output video signal transmitted from the receiver circuit 14 to the mixer circuit 24 is equal to a predetermined amplitude selected for preventing saturation of the elements in the circuit per FIG. 1.

The AGC circuit 30, comprises a programmable current generator 27 and a comparator 29. The voltage potential at the wiper of a potentiometer 31, having one end connected to a power supply and the other end connected to ground potential is provided as the reference input to comparator 29. The video signal from mixer 24 is provided to the other input of the comparator. Whenever the signal along conductor 44′ is less than the predetermined voltage at the wiper of potentiometer 31 the current generator 27 is programmed for providing current along conductor 32 to multiplexer 26. When the output signal of flip-flop circuit 20 is in its initial condition the multiplexer 26 couples the current signal from AGC circuit 30 to capacitor 34 and buffer amplifier 36. The output of buffer amplifier 36 is then coupled via multiplexer 28 to receiver circuit 14.

The receiver circuit is designed for varying the amplitude of the video signal provided along conductor 42 to mixer 24 responsive to the voltage signal conducted through multiplexer 28. The current from the AGC circuit 30 is selected for causing the entrant surface responsive video signal transmitted from receiver circuit 14 to have a predetermined amplitude for preventing saturation of the mixer circuit 24 and the AGC circuit 30.

When the signal from video detector 22 causes flip-flop circuit 20 to change from its initial condition, a signal along conductor 56 to multiplexer 26 causes the increased amplitude output signal from AGC circuit 30 to be coupled to capacitor 38 and buffer amplifier 40 instead to capacitor 34 and amplifier 36 as heretofore. Likewise, a signal along conductor 58 causes the multiplexer 28 to couple the increased amplitude signal from buffer amplifier 40 to receiver circuit 14. The gain of receiver circuit 14, responsive to the amplitude of the signal from multiplexer 28, is increased for providing greater amplification for the echo responsive signal reflected from the acoustic discontinuity remote from the entrant surface 18 of the workpiece W.

The entrant surface and rear wall responsive video signals appearing along conductor 42 are of equal amplitude but 180° out of phase with each other. The mixer circuit 24, as described below, shifts the phase of one of the video signals by 180°.

In a preferred embodiment mixer circuit 24 comprises a type SG 3402 variable gain, wideband amplifier/multiplier manufactured by Silicon General Incorporated, Westminster, Calif. which device, responsive to a signal from flip-flop circuit 20 along conductor 60, causes the input signal received by mixer circuit 24 along conductor 42 to be shifted in phase by 180° at the conductor 44. In this manner, since the output video signals from receiver circuit 14 transmitted along conductor 42 are of equal amplitude due to the AGC circuitry as described above, the signals along conductor 44 will appear as shown in FIG. 2, trace b. Waveform 68 corresponds to the entrant surface responsive video signal amplified by receiver 14 responsive to the voltage signal at the output voltage signal of buffer amplifier 36 for preventing saturation of the mixer circuit 24 and the AGC circuit 30. Waveform 70 corresponds to the rear wall responsive video signal shifted by 180° in mixer circuit 24 amplified by receiver circuit 14 responsive to the output voltage signal of buffer amplifier 40.

Operation of the Circuit Per FIG. 1

In operation clock 12 simultaneously transmits a timing pulse to pulser 10 and a reset pulse to flip-flop circuit 20. The flip-flop circuit 20 is reset, causing the multiplexers, 26, 28 and mixer circuit 24 to assume their initial conditions. Concurrently therewith, the pulser 10 causes transducer probe 16 to transmit an ultrasonic energy search into workpiece W. As described above, the probe 16 receives reflected signal responsive to the entrant surface and rear wall of the workpiece W which are 180° out of phase with each other and of different amplitudes as shown in FIG. 2, trace a. The first received echo responsive signal conducted from probe 16 to receiver circuit 14 is amplified by the receiver circuit 14 responsive to the voltage signal from buffer amplifier 36. The output video signal from receiver circuit 14 is transmitted along conductor 42 to mixer circuit 24. The mixer circuit 24 transmits the video signal represented by waveform 60 along conductor 44' without changing the phase to the AGC circuit 30 causing the amplitude of the signal represented by waveform 68 and transmitted along conductor 44 to be of a predetermined amplitude. The video detector circuit 22 detects the receipt of a video pulse which is less than the predetermined threshold value Vc. The threshold level Vc is adjustable by varying the position of the wiper of potentiometer 52. The potentiometer 52 is connected at one end to a negative power supply and at its other end to ground potential. The AGC circuit 30 provides a direct current current signal to multiplexer 26 as described above.

When the first echo responsive signal represented by waveform 68 reaches the threshold level Vc at point 72, the video detector provides a first pulse to set the flip-flop circuit 20 and to initiate a time interval measuring circuit (not shown). The flip-flop circuit 20 changes its output condition and transmits a signal along conductors 56, 58 and 60 responsive to the pulse from the video detector circuit 22, causing mixer circuit 24 to shift by 180 degrees the phase of subsequently received video signals. In addition, the multiplexers 26 and 28 change their conditions, coupling now the output signal from AGC circuit 30 to the input of buffer amplifier 40 (instead of amplifier 36) and coupling the output of buffer amplifier 40 via multiplexer 28 to receiver circuit 14.

The phase of the ensuing rear wall responsive video signal is thus shifted by 180° in the mixer circuit 24 and the phase shifted signal is conducted to AGC circuit 30. The direct current current signal from AGC circuit 30 varies the voltage provided to buffer amplifier 40 which voltage is, in turn, provided to receiver circuit 14 via multiplexer 28. The components of the AGC circuit 30 are selected for causing the amplitude of the signal represented by waveform 70 to be of equal amplitude as the signal represented by waveform 68 independent of the distance traveled by the ultrasonic energy signal through the workpiece.

The rear wall responsive signal (waveform 70) upon reaching the threshold level Vc at point 74 causes the video detector circuit 22 to provide a second pulse to the time interval measuring circuit causing the time interval measuring circuit to cease measuring. The time interval measured between the two pulses from video detector 22 is commensurated with the thickness of the workpiece.

Prior apparatus require the use of two video detectors, one having a negative voltage threshold level $V^-$ and the other having a positive voltage threshold level $V^+$, and two AGC circuit one for negative going signals and the other for positive going signals. It will be apparant that if either threshold level $V^+$ or $V^-$ or both vary due to aging of their components, thermal drift or the like, the time interval measurement will no longer be accurate. In the present invention, only one AGC circuit 30 is required since both signals at the output of mixer circuit 24 are of the same polarity. Moreover, the signals represented by the waveforms 68 and 70 substantially coincide with each other since they are of equal amplitude and phase, therefore, any drift of the threshold level Vc does not result in a change in time interval measurement since a shift along the waveform 68 to point 76 will result in an equal shift along waveform 70 to point 78. The present invention, therefore, permits a more accurate thickness measurement using fewer circuit components.

FIG. 3 shows a modification of the circuit per FIG. 1. The receiver circuit 14 in FIG. 1 must be capable of changing gain from a first variable value required for amplifying the entrant surface responsive signal shown as waveform 60 to a second variable value required for amplifying the rear wall responsive signal shown as waveform 62. A receiver circuit of the type described having a wide dynamic range is generally complex and expensive. In FIG. 3, the receiver circuit 14 is replaced by a receiver circuit 48 and an amplifier circuit 46 both circuits having a limited dynamic range. The clock 12 transmits reset signals to flip-flop circuit 20 and timing pulses to pulser circuit 10 causing the probe 16 to periodically transmit ultrasonic search signals into the workpiece W. Potentiometer 50, having one end connected to a power supply and the other end connected to ground has its wiper 54 connected to one input of multiplexer 28. The wiper 54 is adjusted so that the gain of amplifier circuit 46 is fixed at a predetermined value for causing the gain of receiver circuit 48, responsive to the output signal from buffer amplifier 40, to be such that the amplitude of the entrant surface responsive video signal transmitted along conductor 42 has a predetermined amplitude. When the entrant surface signal along conductor 42 and hence along conductor 44 is less than or equal to the threshold level Vc, as determined by the position of potentiometer 52, a pulse is transmitted from the video detector circuit 22 to flip-flop circuit 20. The potentiometer 52 is connected at one end to a negative power supply and at its other end to ground. The flip-flop circuit 20 changes its output condition as described in conjunction with FIG. 1. Hence, the buffer amplifier 36 is connected to amplifier circuit 46. Simultaneously, the mixer circuit 24 shifts the phase of the subsequently received rear wall responsive video signal by 180 degrees. The gain of amplifier circuit 46 is varied in the manner described in connection with receiver circuit 14 in FIG. 1.

The improvement in FIG. 3 resides in the fact that the gain of receiver circuit 48 and that of amplifier circuit 46 are independently adjusted. The receiver circuit 48 gain is adjusted responsive to the entrant surface responsive signal and the gain of amplifier 46 is adjusted responsive to the rear wall responsive signal. In this manner, the dynamic range of the amplifier circuit 46 is changed from a predetermined fixed value responsive to the position of wiper 54 of potentiometer 50 to a value determined by the AGC loop comprising amplifier 36. The gain of receiver circuit 48 is dependent upon the value determined by the AGC loop comprising buffer amplifier 40 which exhibits small variations, thus requiring a smaller dynamic range for receiver circuit 48 and permitting a less expensive and less complex design.

While the above description refers to a pulse-echo ultrasonic thickness measuring apparatus for measuring the distance between the frontal surface and rear wall of a workpiece, the distance between any two acoustic discontinuities can be measured by the addition of gating circuits in the video detector circuit.

While in the foregoing description an electrical circuit for use in a pulse-echo ultrasonic measuring apparatus has been described and illustrated, it will be apparent to those skilled in the art that many variations and modifications of the circuit may be made without deviating from the broad principle of the invention which shall be limited solely by the scope of the appended claims.

What is claimed is:

1. An electrical circuit for an ultrasonic pulse-echo measuring apparatus comprising:
   means for transmitting an ultrasonic search signal into a workpiece and receiving a first and a second echo responsive signal in response to the transmission of such search signal, said second signal as received being of lower amplitude than said first signal and being phase inverted relative to said first signal;
   receiving means including signal amplifying means coupled for receiving said echo responsive signals and providing said signals after amplification to a time interval measuring circuit, and
   control means include phase inversion means coupled between said receiving means and said time interval measuring circuit for causing, in response to said amplified first echo responsive signal attaining a predetermined amplitude, said receiving means to be conditioned for increased amplification to cause said second echo responsive signal to attain said predetermined amplitude, and causing furthermore said phase inversion means to be conditioned for effecting said second echo responsive signal to be phase inverted with respect to said first echo responsive signal so as to be of the same phase as said first echo responsive signal when provided to said measuring circuit.

2. An electrical circuit as set forth in claim 1, said control means being arranged for causing said second echo responsive signal to be phase inverted subsequent to attaining said predetermined amplitude.

3. An electrical circuit as set forth in claim 1, said control means including a detector means producing a signal responsive to one of said echo responsive signals attaining said predetermined amplitude.

4. An electrical circuit as set forth in claim 3, said phase inversion means comprising a mixer coupled for receiving said signal from said detector means for providing phase inversion.

5. An electrical circuit as set forth in claim 3, said control means comprising further:
   an automatic gain control circuit coupled to said phase inversion means for receiving said first and said phase inverted second echo responsive signal;
   first multiplexer means coupled to said automatic gain control circuit for receiving the output signal of said automatic gain control circuit for providing said automatic gain control output signal to a first amplifier means, and
   second multiplexer means coupled to said first amplifier means for providing the output signal of said first amplifier means to said receiving means for causing said first echo responsive signal to attain said predetermined amplitude.

6. An electrical circuit as set forth in claim 5, said control means comprising additionally:
   second amplifier means coupled to said first multiplexer means for receiving, responsive to said signal produced by said detector means, the output signal from said automatic gain control circuit;
   said second amplifier means being coupled via said second multiplexer means, responsive to said signal produced by said detector means, to said receiving means for causing said second echo responsive signal to attain said predetermined amplitude.

* * * * *